United States Patent
Nagamune et al.

(10) Patent No.: US 7,198,945 B2
(45) Date of Patent: Apr. 3, 2007

(54) CELL HAVING MODIFIED CELL MEMBRANE

(75) Inventors: Teruyuki Nagamune, Kawagoe (JP); Chika Itoh, Kawasaki (JP); Tohru Yasukohchi, Yokohama (JP); Syunsuke Ohhashi, Yokohama (JP); Kazuhiro Kubo, Kawasaki (JP)

(73) Assignees: Teruyuki Nagamune, Saitama (JP); NOF Corporation, Tokyo (JP)

( * ) Notice: Subject to any disclaimer, the term of this patent is extended or adjusted under 35 U.S.C. 154(b) by 523 days.

(21) Appl. No.: 10/211,587

(22) Filed: Aug. 5, 2002

(65) Prior Publication Data

US 2003/0114523 A1 Jun. 19, 2003

(30) Foreign Application Priority Data

Aug. 9, 2001 (JP) ............................. 2001-241843

(51) Int. Cl.
*C12N 5/00* (2006.01)
(52) U.S. Cl. ....................... 435/325; 435/243
(58) Field of Classification Search ............... 435/243, 435/325
See application file for complete search history.

(56) References Cited

U.S. PATENT DOCUMENTS

| 6,051,207 A | 4/2000 | Klaveness et al. |
| 6,261,537 B1 | 7/2001 | Klaveness et al. |
| 6,264,914 B1 | 7/2001 | Klaveness et al. |
| 6,264,917 B1 | 7/2001 | Klaveness et al. |
| 6,309,633 B1 | 10/2001 | Ekwuribe et al. |
| 2001/0016587 A1 | 8/2001 | Klaveness et al. |
| 2002/0102215 A1 | 8/2002 | Klaveness et al. |
| 2002/0102217 A1 | 8/2002 | Klaveness et al. |
| 2002/0165205 A1 | 11/2002 | Kubo et al. |

FOREIGN PATENT DOCUMENTS

| EP | 1241172 | 9/2002 |
| JP | 2002-037883 | 2/2002 |
| WO | 97/32617 | 9/1997 |
| WO | 98/18501 | 5/1998 |
| WO | 00/78302 | 12/2000 |

OTHER PUBLICATIONS

English Language Abstract of JP 2002-037883.
Bendas et al., "Targetability of Novel Immunoliposomes Prepared by a New Antibody Conjugation Technique", International Journal of Pharmaceutics, vol. 181, No. 1, Apr. 20, 1999, pp. 79-93.
Torchilin et al., "p-Nitrophenylcarbonyl-PEG-PE-liposomes: Fast and Simple Attachment of Specific Ligands, Including Monoclonal Antibodies, to Distal Ends of PEG Chains Via p-nitrophenylcarbonyl Groups", Biochimica Et Biophysica Acta, vol. 1511, No. 2, Apr. 2, 2001, pp. 397-411.
M. Edward Medof et al., "Cell-Surface Engineering with GPI-Anchored Proteins", FASEB, vol. 10, pp. 574-586 (1996).
Christina L. Van Broekhoven et al., "Engrafting Costimulator Molecules onto Tumor Cell Surfaces with Chelatro Lipids: A Potentially Convenient Approach in Cancer Vaccine Development", The Journal of Immunology, vol. 164, pp. 2433-2443 (2000).
Polymer Preprints, Japan, vol. 47, No. 10, pp. 2499-2500 (1998), accompanied by an English Language Abstract.
Tanpaku-shitsu, kakusan, kohso,vol. 45, No. 11, pp. 1859-1864 (2000), accompanied by an English Language Abstract.

*Primary Examiner*—Leon B Lankford, Jr.
(74) *Attorney, Agent, or Firm*—Greenblum & Bernstein, P.L.C.

(57) ABSTRACT

A cell in which a reaction product of a substance to be modified and an amphipathic compound is non-covalently bound to a cell membrane, wherein said compound has the following features:
(1) having one or more aliphatic hydrocarbon groups at one end;
(2) having one or more portions containing a hydrophilic group in a molecule; and
(3) having one or more reactive functional groups which are capable of covalently binding with the substance to be modified at an end different from the end in the above (1).

8 Claims, 4 Drawing Sheets

CELL HAVING MODIFIED CELL MEMBRANE

TECHNICAL FIELD

The present invention relates to a cell which is modified with a physiologically active substance or a probe. More specifically, the present invention relates to a cell in which a reaction product of a physiologically active substance or a probe and an amphipathic compound is non-covalently bound to the cell membrane.

BACKGROUND ART

The layer of a cell membrane surface consisting of sugar chains and proteins is a site for the cell to express a response to the external environment, such as intercellular recognition. Since molecular recognition and the conversion of information are performed at this site, it is thought that modifying the property of cell membrane surfaces enables diversification of the cell recognition. For example, studies have been conducted to non-individualize cells by modifying the cell membrane surfaces with synthetic polymers.

Japanese Patent Unexamined Publication (Kohyo) No. 2000-507849 discloses a method for covalently modifying cell surfaces by allowing biologically compatible polymers to react with functional groups present on the cell surfaces. Another method for modifying cell surfaces with GPI-anchored protein is reported in The FASEB Journal, 10, 574–586 (1996). Moreover, Polymer Preprints, Japan, 47, 10, 2499–2500 (1998) and Protein/Nucleic Acid/Enzyme (Tanpaku-shitsu, Kakusan, Kohso), 45, 11, 1859–1864 (2000) disclose a method for modifying cell surfaces, which comprises the step of allowing the reactive groups of the polymer ends of polyacrylamides, used as water-soluble polymers, to react with membrane proteins or sugar chains; a method for modifying cell surfaces through binding of ligands to receptors on the cell membranes; and a method for modifying cell surfaces using hydrophobic anchors.

As described above, several methods are known to modify cell surfaces by binding reactive groups of polymer ends to cell membrane proteins and sugar chains. However, such a direct chemical modification on cell membranes may alter properties of substances on the cell surfaces or may damage the cells. Further, the method using GPI-anchored protein has problems in that GPI-anchored proteins are hardly obtainable, and therefore its applicability is limited. Furthermore, by the method using hydrophobic anchors, cell surfaces are modified only with polyacrylamide chains. Although the method successfully achieves suppression of cell aggregation, stability after modification becomes poor, and it has not been verified that polyacrylamide chains can be immobilized on the cell membrane surfaces. Moreover with this method, it is impossible to bind physiologically active substances to cell surfaces.

The Journal of Immunology, 2433–2443 (2000) discloses a method which comprises the steps of anchoring chelate compounds containing hydrocarbon groups to cell membranes, and then allowing physiologically active substances to ionically bind to the chelate compounds. However, the method has problems in that since physiologically active substances are ionically bound to cell membranes, the binding is susceptible to changes of salt concentration or pH and is consequently unstable, and its applicability to cells is also limited. In addition, since the chelate compounds is highly lipophilic as they contain no hydrophilic group and the compounds can hardly be uptaken by cells, a means including preparation of liposomes and their fusion with cells has been used for intracellular incorporation of the compounds. However, the modification of cell membranes by this means is not convenient.

As explained above, no method has been known to date by which properties of cell membranes are modified by covalently binding physiologically active substances or the like to cell membranes without causing any damage to the cells.

SUMMARY OF THE INVENTION

An object of the present invention is to provide a cell whose membrane is modified with a substance to be modified, such as a physiologically active substance or a probe. Another object of the present invention is to provide means for efficiently modifying cells, while avoiding the above-mentioned conventional problems, and causing no damage to the cells.

The inventors of the present invention conducted various studies to achieve the foregoing objects. As a result, the inventors found that cell membranes can be modified non-covalently by using reaction products obtained from reaction between substances to be modified, such as a physiologically active substance or a probe, and amphipathic compounds; and that such modification can be very efficiently performed without causing any damage to cells by using a particular class of amphipathic compounds having aliphatic hydrocarbon groups. The present invention was achieved on the basis of these findings.

The present invention thus provides a cell in which a reaction product of a substance to be modified and an amphipathic compound is non-covalently bound to a cell membrane wherein said compound has the following characteristics:

(1) having one or more aliphatic hydrocarbon groups at one end;

(2) having one or more portions containing a hydrophilic group in a molecule; and (3) having one or more reactive functional groups which are capable of covalently binding with the substance to be modified at an end different from the end in the above (1).

According to preferred embodiments of the present invention, provided are the aforementioned cell wherein the substance to be modified is a physiologically active substance or a probe; and the aforementioned cell wherein the cell is an animal cell.

According to further preferred embodiments of the present invention, provided are the aforementioned cell wherein the aliphatic hydrocarbon group is a residue of a compound having one or more aliphatic hydrocarbon groups having 11 to 18 carbon atoms; the aforementioned cell wherein the aliphatic hydrocarbon group is a residue of a compound having one or more oleyl groups or unsaturated aliphatic hydrocarbon groups having 17 carbon atoms; and the aforementioned cell wherein the hydrophilic group is a residue of a compound having a polyoxyalkylene group.

According to a particularly preferred embodiment of the present invention, provided is the aforementioned cell wherein the amphipathic compound is represented by the following general formula (1):

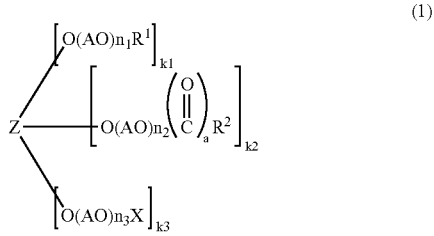

(1)

wherein Z represents a residue of a compound having 2 to 10 hydroxyl groups; AO represents an oxyalkylene group having 2 to 4 carbon atoms; $R^1$ represents a hydrogen atom or a hydrocarbon group having 1 to 3 carbon atoms; $R^2$ represents a residue of a compound having an aliphatic hydrocarbon group having 7 to 22 carbon atoms; X represents a group having one or more reactive functional groups selected from the group consisting of succinimide group, maleimide group, amino group, carboxyl group, aldehyde group, glycidyl group, and thiol group; "a" represents 0 or 1; n1, n2, and n3 represent an average number of added moles of an oxyalkylene group having 2 to 4 carbon atoms, and each numerical number represented by n1, n2, n3, k1, k2, and k3 satisfies the following conditions:

$0 \leq n1$, $n2 \leq 500$, $2 \leq n3 \leq 500$, and $2 \leq n1+n2+n3 \leq 500$ $0 \leq k1 \leq 8$, $1 \leq k2 \leq 4$, $1 \leq k3 \leq 4$, and $2 \leq k1+k2+k3 \leq 10$.

According to further preferred embodiment of the above present invention, provided are the aforementioned cell wherein $R^2$ is a residue of a compound having one or more linear aliphatic hydrocarbon groups having 11 to 18 carbon atoms; the aforementioned cell wherein $R^2$ is a residue of a compound having one or more oleyl groups or an unsaturated aliphatic hydrocarbon group having 17 carbon atoms; and the aforementioned cell wherein $R^2$ is a group represented by the following general formula (2):

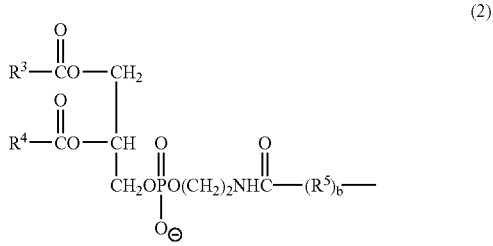

(2)

wherein each of $R^3$ and $R^4$ independently represents a hydrocarbon group having 7 to 21 carbon atoms; $R^5$ represents a hydrocarbon group having 2 to 4 carbon atoms; and b represents 0 or 1.

From another aspect of the present invention, provided are the above amphipathic compound which is used for allowing a reaction product of the amphipathic compound and a physiologically active substance or a probe, to bind non-covalently to a cell membrane; and a use of the above amphipathic compound for modifying a cell membrane.

According to the present invention, also provided is a method for modifying cell membranes which comprises the steps of: (1) allowing a physiologically active substance or a probe to react with the aforementioned amphipathic compound; and (2) allowing the reaction product obtained in the above step (1) to non-covalently bind to a cell membrane.

BEST MODE FOR CARRYING OUT THE INVENTION

Figure 1:
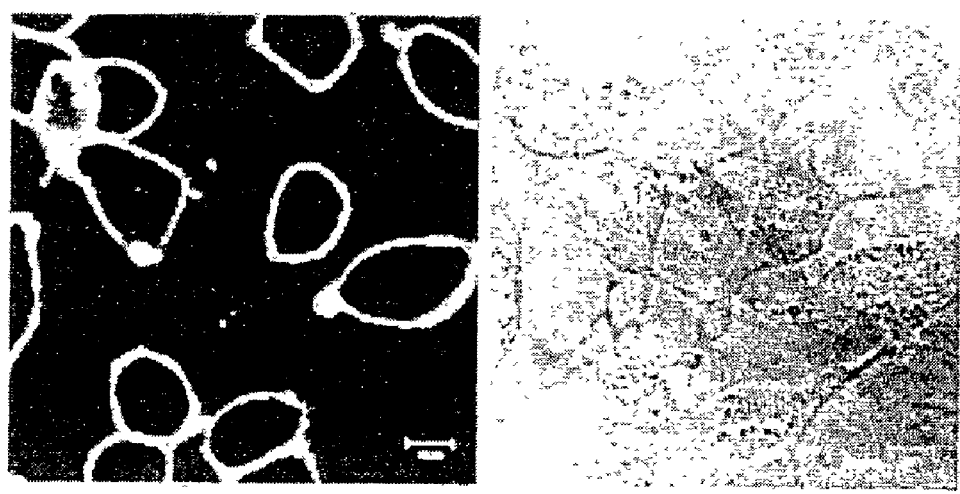
FIG. 1 shows microscopic photographs of mouse fibroblast cell line NIH3T3 (Example 2) whose membranes were modified with fluorescein-labeled streptavidin bound to polyethylene oxide oleylether (n=90, average molecular weight of 4,400)-biotin conjugates.

The cells of the present invention are characterized in that a reaction product of a substance to be modified and an amphipathic compound having a reactive functional group capable of covalently binding with the substances to be modified, is bound non-covalently to cell membranes. Any cell that has a cell membrane composed of a class of phospholipids can be used. Examples of such cells include animal cells, protoplast plant cells, and microorganisms. A preferred example is an animal cell. For example, an action for immunological activation can be induced by modifying the surfaces of immunocytes with physiologically active substances.

Types of substances for modification to be bound to cell membranes are not particularly limited, and any substances can be used so far that the substance has at least one functional group which is capable of covalently binding with an amphipathic compound. Examples of functional groups capable of forming covalent bond include an amino group, a hydroxyl group, a thiol group, and a carboxyl group. As a compound to be modified, preferably, a physiologically active substance, a probe or the like can be used. Further, two or more types of substances to be modified can be bound to the cells of the present invention. For example, a physiologically active substance and a probe may be bound in combination to a cell.

Types of physiologically active substances are not particularly limited. For example, various substances from low molecular substances to high molecular substances, such as amino acids, oligopeptides, proteins, nucleotides, oligonucleotides, polynucleotides, glycoproteins, monosaccharides, polysaccharides, and vitamins, in addition to compounds as effective ingredients of medicaments, such as enzyme inhibitors, receptor/antagonists or agonists can be used. Preferable examples of physiologically active substances include antibodies, adhesive molecules, receptors, and cytokines such as growth factors. The term "physiologically active substance" used in the present specification should be construed in the broadest sense so as to encompassing a substance which can induce at least one vital reaction, a biologically related substance which can be used in vivo and the like, and the term should not be construed in any limiting manner.

As the probes, for example, probes for detecting amino acids, oligopeptides, polypeptides, proteins, nucleotides, oligonucleotides, polynucleotides, enzyme substrates, metal ions and the like may be used. Fluorescent probes, luminescent probes, magnetic probes, radioactive probes, and fine particle probes such as gold colloids may be used. However, probes are not limited to those used for detecting the above substances and those provided with the above detection means.

The amphipathic compound has the following characteristics:

(1) having one or more aliphatic hydrocarbon groups at one end;
(2) having one or more portions containing a hydrophilic group in a molecule; and
(3) having one or more reactive functional groups capable of covalently binding with the substance to be modified, at an end different from the end in the above (1).

Examples of the hydrophilic groups include synthetic or natural water-soluble compounds, preferably, residues of water-soluble high-molecular compounds. Examples of the water-soluble compounds which provide hydrophilic groups include polyalkylene glycol, polysaccharide, polylactic acid, polyvinylalcohol, polyacrylic acid, and polyacrylamide, preferably, polyalkylene glycol, polysaccharide, polylactic acid, and polyvinylalcohol, and more preferably, polyalkylene glycol.

Aliphatic hydrocarbon groups may be groups derived from synthetic or natural aliphatic hydrocarbons, preferably saturated or unsaturated linear or branched aliphatic hydrocarbon groups having 6 to 24 carbon atoms (in the specification, when a molecule or a functional group is referred to as "unsaturated," the number of double bonds or triple bonds present therein is not specifically limited, and it may contain a combination of a double bond and a triple bond); more preferably, groups containing saturated or unsaturated aliphatic hydrocarbon groups having 11 to 18 carbon atoms; and further more preferably groups containing an oleyl group or an unsaturated hydrocarbon group having 17 carbon atoms. A single hydrocarbon group may be used alone or two or more types may be used in combination. When two or more hydrocarbon groups are used in combination, a manner of combination is not limited.

Reactive functional group in the amphipathic compound may preferably be provided at an end of a hydrophilic portion. Any reactive functional group may be used, so far that the group can react with a functional group such as an amino group, a carboxyl group, a thiol group, and a hydroxyl group of a physiologically active substances. Examples of such reactive functional groups include a succinimide group, a maleimide group, an amino group, a carboxyl group, an aldehyde group, a glycidyl group, thiol group and the like.

As an amphipathic compound, a compound represented by the formula (1) can be used. Specifically, examples of a residue of a compound having 2 to 10 hydroxyl groups, represented by Z, include residues of compounds such as ethylene glycol, propylene glycol, glycerin, diglycerin, pentaerythritol, triglycerin, tetraglycerin, pentaglycerin, hexaglycerin, heptaglycerin, octaglycerin and the like. As Z, preferably, a residue of a compound having 2 to 8 hydroxyl groups can be used.

AO is an oxyalkylene group having 2 to 4 carbon atoms, preferably 2 or 3 carbon atoms. Examples of AO include an oxyethylene group, an oxypropylene group, an oxytrimethylene group, an oxybutylene group, an oxytetramethylene group and the like. In particular, oxyethylene groups are preferred among these groups. In a molecule, the numbers of oxyalkylene groups corresponding to "n" are present. A single type of oxyalkylene group may be used alone, or two or more types may exist be used in combination. When two or more types are used in combination, a manner of the combination is not limited. Further, the oxyalkylene groups may have a block- or random-polymer chain. When a rate of the oxyethylene groups based on the total oxyalkylene groups is low, water solubility may sometimes be reduced. Accordingly, it is preferred that the rate of the oxyethylene groups based on the total oxyalkylene groups ranges from 50 to 100 mol %.

In the formula (1), $n1+n2+n3$ represents an average number of the moles of added oxyalkylene groups. The sum thereof may be in the range of 2 to 500, for example, and preferably 8 to 300, and more preferably 12 to 200. The number of the added moles can be chosen depending on the balance between hydrophilicity and hydrophobicity, for example, between the oxyalkylene groups and hydrophobic groups of $R^1$ or $R^2$. When k2 is 2 or more, or $R^2$ is a residue of a phospholipid compound, it is preferred that 2 or more chains of hydrophobic aliphatic hydrocarbon groups are present and the average number of the moles of added oxyalkylene groups, i.e., $(n1+n2+n3)$, ranges from 20 to 500, and further preferably 30 to 200.

The sum of $k1+2+k3$ in the above formula (1) corresponds to the number of branched chains of Z, and preferably an integer of from 2 to 10, preferably from 2 to 4. When the sum of $k1+k2+k3$ is less than 2, a compound is not obtainable which has a hydrophobic group as an aliphatic hydrocarbon group at one end, and a reactive functional group at the other end, which may result in disadvantageous for modification of cell surfaces. In addition, when the sum of $k1+k2+k3$ is greater than 10, the molecule becomes bulky with three-dimensional overspreads, which may result in a failure of stable surface modification due to steric hindrance.

In the above formula (1), k1 represents the total number of residues at the branched ends of the polyalkylene oxide, being hydrogen atoms or hydrocarbon groups having 1 to 3 carbon atoms (more specifically, methyl group, ethyl group, n-propyl group, or isopropyl group), and is an integer of from 0 to 8. In the above formula (1), k2 represents the number of bound residues of a compound having aliphatic hydrocarbon groups with 8 to 22 carbon atoms at the ends of the polyalkylene oxide, and is an integer of from 1 to 4. When k2 is 0, cell membranes cannot sometimes be modified due to the absence of hydrophobic groups; and when k2 is 5 or more, the molecule becomes too bulky to be successfully anchored into cell membranes.

In the above formula (1), "a" represents 0 or 1. When "a" is 0, it means that a residue of a compound having an aliphatic hydrocarbon group, represented by $R^2$, is ether-linked to the end of the polyalkylene oxide residue. When "a" is 1, it means that a residue of a compound having an aliphatic hydrocarbon group, represented by $R^2$, is ester-linked by means of a carbonyl group to the end of the polyalkylene oxide residue.

In the above formula (1), k3 represents a polyalkylene oxide residue wherein a group having a reactive group represented by X is bound to the terminal residue, and is an integer of from 1 to 4, preferably 1 to 3. When k3 is 2 or more, as reactive groups included in X, a single type group may be used alone, or two or more types may be used in combination. When two or more types of groups are used, the same or different types of physiologically active substances may be bound to the groups and introduced to cell membranes.

In the above formula (1), $R^1$ represents a hydrogen atom, a methyl group, an ethyl group or a linear or branched propyl group. When k2 is 1 or more, an aliphatic hydrocarbon group represented by $R^2$ acts as a hydrophobic group of the compound of the formula (1).

In the above formula (1), $R^2$ represents a residue of a compound having an aliphatic hydrocarbon group having 7 to 22 carbon atoms. Preferably, $R^2$ represents a residue of a saturated or unsaturated linear or branched aliphatic hydrocarbon group having 7 to 22 carbon atoms, or a residue of a compound containing a phosphate group which has one or more saturated or unsaturated linear or branched aliphatic hydrocarbon groups having 7 to 22 carbon atoms. Specific examples of $R^2$ include, when "a" is 0, a saturated or unsaturated linear or branched hydrocarbon group, such as a capryl group, a decyl group, a lauryl group, a myristyl group, a myristoleyl group, a palmityl group, a palmitoleyl group, a stearyl group, an isostearyl group, an oleyl group, a linoleyl group, an arachyl group, an arachidyl group, a behenyl group, and erucayl group. Preferably, $R^2$ represents a saturated or unsaturated aliphatic hydrocarbon group having 10 to 20 carbon atoms, or a phospholipid residue having a saturated or unsaturated aliphatic hydrocarbon group with 10 to 20 carbon atoms; more preferably, a saturated or unsaturated linear aliphatic hydrocarbon group having 11 to 18 carbon atoms, or a phospholipid residue having a saturated or unsaturated linear hydrocarbon group with 11 to 18 carbon atoms; and most preferably, a saturated or unsaturated linear aliphatic hydrocarbon group having 18 carbon atoms, or a phospholipid residue having a saturated or unsaturated linear aliphatic hydrocarbon group having 17 carbon atoms. Examples of the phospholipids include phosphatidylethanolamine, phosphatidylglycerol, and phosphatidylserine. When "a" is 1, specific examples of $R^2CO$ include acyl groups which are derived from saturated or unsaturated, linear or branched fatty acids, such as caprylic acid, capric acid, lauric acid, myristic acid, myristoleic acid, palmitic acid, palmitoleic acid, stearic acid, isostearic acid, oleic acid, linolic acid, arachic acid, behenic acid, and erucic acid, and preferably an acyl group derived from oleic acid.

In the above formula (1), X represents a group having a reactive functional group, such as a succinimide group, a maleimide group, an amino group, a carboxyl group, an aldehyde group, a glycidyl group or a thiol group. A mode of binding of X to the end of a polyalkylene oxide residue is not particularly limited, and ordinary modes of binding such as those reported in JMS-REV. MACROMOL. CHEM. PHYS., C25(3), 325–372 (1985) can be used. For convenient introduction of the above reactive group, preferable introduction may be performed via a divalent hydrocarbon group, an ester bond, or an amide bond. Examples of the hydrocarbon groups used for the above purpose include a methylene group, an ethylene group, a propylene group, a butylene group, a pentylene group, a hexylene group and the like, or a residue of a cyclic compound such as a phenylene group and the like. Ester bond may be derived from monocarboxylic acid or dicarboxylic acid. Examples of the dicarboxylic acid include succinic acid, glutaric acid, maleic acid and the like. Examples of the amide bond include those derived from ethylamide, propylamide and the like.

The above formula (2) represents a residue of a phosphate group-containing compound, i.e., a phosphatidylethanolamine-containing residue, having one or more saturated or unsaturated linear or branched aliphatic hydrocarbon groups with 7 to 21 carbon atoms. In the above formula (2), each of $R^3$ and $R^4$ independently represents a saturated or unsaturated, linear or branched aliphatic hydrocarbon group having 7 to 21 carbon atoms, preferably, a saturated or unsaturated linear hydrocarbon group having 11 to 17 carbon atoms, more preferably an unsaturated hydrocarbon group having 17 carbon atoms. As for $R^3$ and $R^4$, acyl groups derived from fatty acid may normally be used as $R^3CO$ and $R^4CO$. Specific examples of $R^3CO$ and $R^4CO$ include hydrocarbon groups having acyl groups derived from saturated or unsaturated, linear or branched fatty acid, such as caprylic acid, capric acid, lauric acid, myristic acid, myristoleic acid, palmitic acid, palmitoleic acid, stearic acid, isostearic acid, oleic acid, linolic acid, arachic acid, behenic acid, erucic acid and the like.

$R^3$ and $R^4$ may be the same or different. When respective carbon numbers of $R^3$ and $R^4$ are greater than 21, binding to cell membranes may sometimes be failed due to high hydrophobicity and low flexibility; and when the respective carbon numbers are less than 7, the molecule may sometimes be unloaded from the membrane after binding due to weak hydrophobicity. When $R^2$ is a residue of a phospholipid-containing compound, represented by the formula (2), the residue has higher stability after cell membrane modification attributable to the two chains of acyl groups than a residue with a single chain of an acyl group, and the molecule being anchored to a cell membrane may hardly be unloaded from the cell membrane.

In the above formula (2), $R^5$ represents a divalent hydrocarbon group having 2 to 4 carbon atoms. The group may be linear, branched, cyclic or any combination thereof, and may be either saturated or unsaturated. Specific examples include —$CH_2CH_2$—, —$(CH_2)_3$—, or —$(CH_2)_4$— group.

Symbol "b" represents 0 or 1.

In the cells of the present invention, when the amphipathic compounds have one or more asymmetric carbons, any stereoisomers in a pure form such as optically active compounds or diastereoisomers, any mixtures of the stereoisomers, racemates and the like can be used as the amphipathic compounds. When olefinic double bonds are contained, compounds in E or Z-configuration in a pure form, or any mixtures thereof may be used.

The modification method of cell membranes provided by the present invention is characterized to comprise the steps of: (1) allowing a physiologically active substance or a probe to react with the above amphipathic compound; and (2) allowing the reaction product obtained in the above step (1) to non-covalently bind to cell membrane.

Types of solvents used in the above reaction step (1) are not particularly limited, so far as they are not involved in the reaction. A buffer or an isotonic solution thereof such as a phosphate buffer, a borate buffer, Tris buffer, an acetate buffer, a carbonate buffer, and "Good" buffer; an organic solvent or a mixture of the above aqueous medium and an organic solvent may be used. They may be used as a single solvent system or a mixed solvent system. To avoid denature or deactivation of a substance to be modified such as a physiologically active substance, an organic solvent which is not involved in the reaction, such as acetonitrile, dimethyl sulfoxide, dimethylformamide and the like, is preferably used. Reaction temperature is not particularly limited, so far as the temperature causes no denature or deactivation of a substance to be modified such as a physiologically active substance. For example, a range of 0 to 100° C. is preferred, and 0 to 40° C. is more preferred. Reaction time normally ranges from approximately 1 min to 48 hours, and preferably 0.5 to 3 hours. After the reaction, a reaction product can be purified by applying ordinary methods for purification of a protein, such as dialysis, ultrafiltration, gel filtration and the like. The reaction product may be used for step (2) without purification.

In step (2), the reaction product obtained in step (1) may be added to culture cells. The reaction product to be used, which is obtained in the above step (1), may be diluted before the addition to 0.1 to 1000 fold of the critical micelle formation concentration (hereinafter abbreviated as CMC), preferably 1 to 500 fold of the CMC, more preferably 10 to 100 fold of the CMC using a cell culture solution or an isotonic solution. Binding of the reaction product obtained in step (1) to the cells may generally be carried out at 0 to 40° C. for 1 sec to 120 min, preferably at 25 to 37° C. for 10 sec to 20 min. In this step, additives may be added, in addition to the reaction product obtained in step (1). After the above reaction product is bound to the cell membranes, the cells are preferably added with an isotonic solution and washed. An isotonic solution used is not particularly limited, so far as it causes no damage to the cells. For example, isotonic solutions such as phosphate buffered saline, cell culture medium and the like can be used.

EXAMPLES

The present invention will be more specifically explained with reference to the following examples. However, the scope of the present invention is not limited to the following examples. Hereinafter, reaction product of a substance to be modified and an amphipathic compound may sometimes be referred to as "conjugate"; modification of cell membranes with the conjugate as "anchoring" to; and succimidyl succinate at the end of the polyethylene oxide as "activated polyethylene oxide" or "active form of polyethylene oxide".

Example 1

Preparation of Polyethylene Oxide Oleylether (n=90, Average Molecular Weight of 4400)-biotin Conjugate Synthesis Example 1: Synthesis of Activated Polyethylene Oxide Oleylether 0.1 mol % sodium acetate was added to 4 g (1 mmol) of polyethylene oxide oleylether (n=90, average molecular weight of 4400), 0.12 g (1.2 mmol) of succinic anhydride was added, and then reaction was conducted at 100° C. for 5 hours. Subsequently, 5 mL of dimethyl formamide and then 0.14 g (1.2 mmol) of N-hydroxysuccinimide (NHSI) were added, followed by stirring at 40° C., and then 0.21 g (2 mmol) of dicyclohexyl carbodiimide was added to obtain activated polyethylene oxide oleylether. After the reaction, crystallization was performed for purification with 25 mL of cool isopropyl alcohol and 50 mL of hexane to obtain 3.5 g of crystals.

Preparation of Polyethylene Oxide Oleylether (n=90, Average Molecular Weight of 4400)-biotin Conjugate 4.4 mg (1 nmol) of the activated polyethylene oxide oleylether (n=90, average molecular weight of 4400) was dissolved in 0.1 mL of dimethyl sulfoxide to prepare a solution of the activated polyethylene oxide oleylether (n=90, average molecular weight of 4400). 1 nmol EZ-Link™ Biotin-PEO-Amine (PIERCE; Cat# 21346) was dissolved in 0.1 mL of dimethyl sulfoxide to prepare a Biotin-PEO-Amine solution. To the Biotin-PEO-Amine solution, the polyethylene oxide oleylether solution (n=90, average molecular weight of 4400) was added to afford a reaction solution. The reaction solution was stirred at room temperature (about 25° C.), and then allowed to stand for 1 hour. 0.02 mL of 1M Tris buffer (pH 8.0) and 0.78 mL of phosphate buffered saline for tissue culture [prepared from "Nissui" powder for Dulbecco's PBS(−) tissue culture (NISSUI PHARMACEUTICAL CO., LTD.; Cat# 05913)] were added to the reaction solution to obtain a solution of polyethylene oxide oleylether (n=90, average molecular weight of 4400)-biotin conjugates.

Example 2

Anchoring of Polyethylene Oxide Oleylether (n=90, Average Molecular Weight of 4400)-biotin Conjugate to Mouse Fibroblast Cell Line NIH$_3$T3

Cultivation of Mouse Fibroblast Cell Line NIH$_3$T3

Mouse fibroblasts NIH$_3$T3 were cultured at 37° C. under 5% CO$_2$ concentration using Dulbecco's Modified Eagle's Medium supplemented with 10% fetal calf serum and Glass bottom Microwell Dishes (35 mm dish, Uncoated, No. 0 Coverslip). The cells were cultured until the culture was approximately 80% confluent for 20 hours to 45 hours. A stock solution of the polyethylene oxide oleylether (n=90, average molecular weight of 4400)-biotin conjugates obtained in Example 1 was diluted 100 fold with Dulbecco's Modified Eagle's Medium to prepare a solution of the polyethylene oxide oleylether (n=90, average molecular weight of 4400)-biotin conjugates. The Glass bottom Microwell Dishes with NIH$_3$T3 cells attached thereto were rinsed with 2 mL of phosphate buffered saline (the same as described above) which was subjected to filtration sterilization beforehand. Then, 0.1 mL of the polyethylene oxide oleylether-biotin conjugate solution was added to the NIH$_3$T3 cells attached on the glass surface and a reaction was performed at 37° C. for 5 min. After the reaction, the cells were washed twice with 2 mL of phosphate buffered saline. Then, 0.1 mL of phosphate buffered saline containing 6.7 nM streptavidin and fluorescein conjugate (Molecular Probes; Cat# S-869) (hereinafter referred to as "fluorescein-labeled streptavidin") was added to the cells, followed by incubation at 37° C. for 20 min.

After the cells were washed 3 times with 2 mL of phosphate buffered saline, 1 mL of phosphate buffered saline was added to the cells to obtain the cells whose membranes were modified with fluorescein-labeled streptavidin bound to the polyethylene oxide oleylether (n=90, average molecular weight of 4400)-biotin conjugate. The modification of the cell membranes was verified by observing the cells under a confocal laser scanning microscope (Leica). Results are shown in Table 1 and FIG. 1. As a results, fluorescence deriving from fluorescein was observed on the cell membranes of all of the cells in the field (1000 magnifications). It was also observed that the polyethylene oxide oleylether (n=90, average molecular weight of 4400)-biotin conjugates were anchored to all of the cell membranes within 5 min. Further, binding of biotin to streptavidin was not inhibited.

Three-Dimensional Observation of Cells

Figure 2:
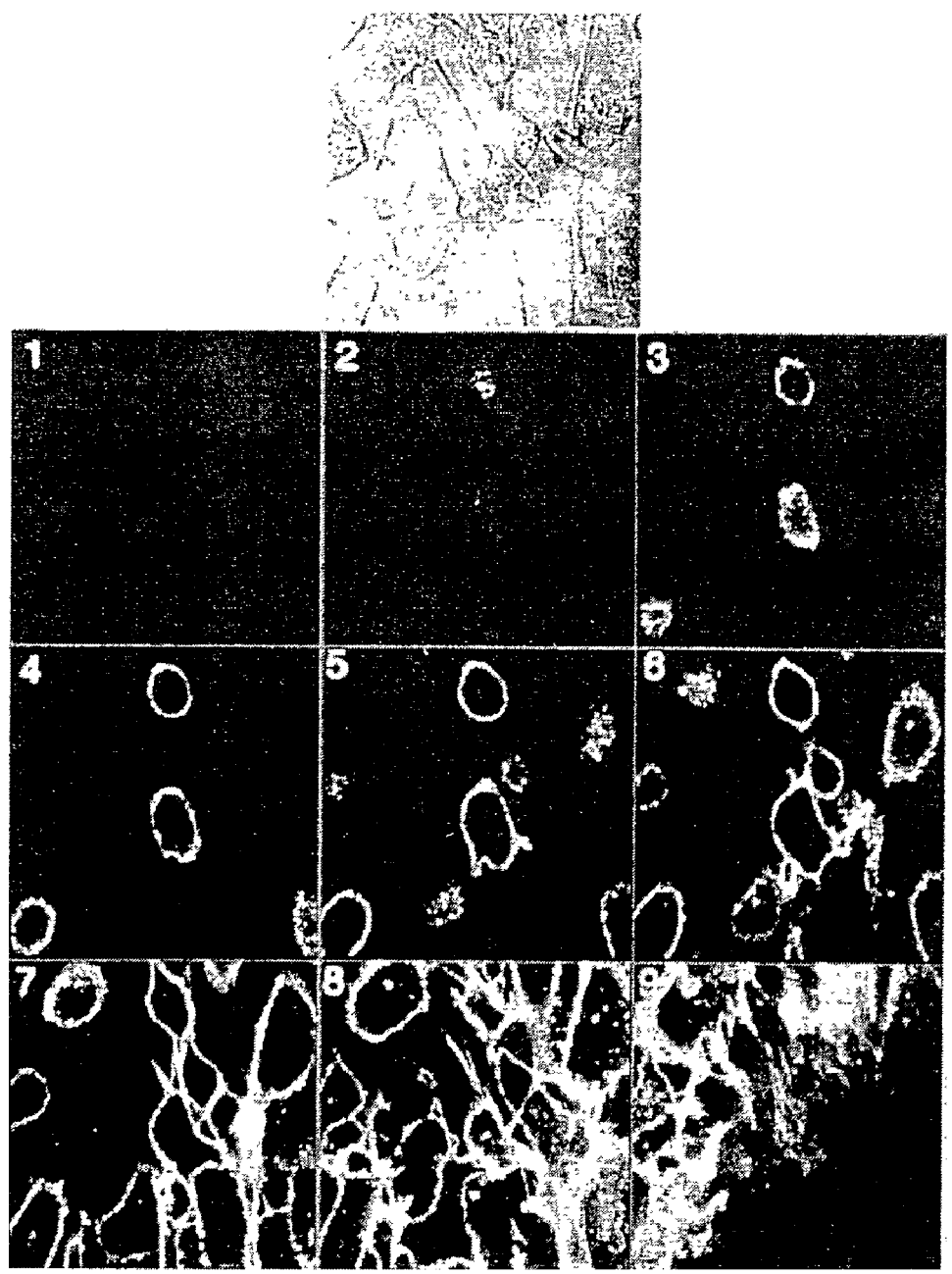
FIG. 2 shows microscopic photographs of sections of mouse fibroblast cell line NIH3T3 (Example 2) whose membranes were modified with fluorescein-labeled streptavidin bound to polyethylene oxide oleylether (n=90, average molecular weight of 4,400)-biotin conjugates.

In a similar manner to Example 2, $NIH_3T3$ cells treated with the polyethylene oxide oleylether (n=90, average molecular weight of 4400)-biotin conjugates were stained with fluorescein-labeled streptavidin, and then for observation, photographed with every 2.3 μm depth in the height direction (Z axis direction) of optical sections having a width of 0.86 μm under a confocal laser scanning microscope. Results are shown in FIG. 2. In all of the cells, fluorescence from fluorescein was specifically observed only in the cell membranes. Accordingly, by the three-dimensional observation of the cells, it was verified that the polyethylene oxide oleylether (n=90, average molecular weight of 4400)-biotin conjugates were bound to all portions of the cell membranes exposed to the liquid phase.

Example 3

Preparation of Polyethylene Oxide Oleylether (n=90, Average Molecular Weight of 4400)-Green Fluorescent Protein EGFP Conjugate 0.1 mL of dimethyl sulfoxide was added to 1.5 μmol of an activated polyethylene oxide oleylether (molecular weight of 4000) obtained in a similar manner to Synthesis Example 1 to obtain a solution of the activated polyethylene oxide oleylether. 0.015 mL of the activated polyethylene oxide oleylether (molecular weight of 4000) solution was added to 0.3 mL of a solution of phosphate buffered saline containing 75 μM of purified green fluorescent protein EGFP (a fusion protein containing a part of the antibody-binding domain of protein G as a purification tag) to afford a reaction solution. The reaction solution was stirred, and then allowed to stand at room temperature (approximately 25° C.) for 1 hour. 0.016 mL of 1M Tris buffer (pH 8.0) was added to the reaction solution to give a stock solution of the polyethylene oxide oleylether (n=90, average molecular weight of 4400)-EGFP conjugates.

Example 4

Anchoring of the Polyethylene Oxide Oleylether (n=90, Average Molecular Weight of 4400)-EGFP Conjugate to Mouse Fibroblast Cell Line $NIH_3T3$ The stock solution of the polyethylene oxide oleylether (n=90, average molecular weight of 4400)-EGFP conjugates was diluted 20 fold with Dulbecco's Modified Eagle's Medium to prepare a solution of polyethylene oxide oleylether (n=90, average molecular weight of 4400)-EGFP conjugates. Similarly to Example 2, the polyethylene oxide oleylether (n=90, average molecular weight of 4400)-EGFP conjugates were anchored to the membranes of $NIH_3T3$ cells, and then the anchoring was verified by observing fluorescence from EGFP under a confocal laser scanning microscope. The results are shown in Table 1. As a result, it was verified that green fluorescent protein EGFP was also anchored to the cell membranes by using the polyethylene oxide oleylether.

Example 5

Anchoring of Polyethylene Oxide Oleylether (n=90, Average Molecular Weight of 4400)-EGFP Conjugate to Chinese Hamster Ovarian Follicle Cell Line CHO Cultivation of CHO Cells Chinese hamster ovarian follicle cell line CHO was cultured at 37° C. under 5% $CO_2$ concentration using Glass bottom Microwell Dishes (35 mm dish, Uncoated, No. 0 Coverslip) in F-12 media (F-12 Nutrient Mixture (GIBCO. BRL; Cat# 21700-075) supplemented with 10% fetal calf serum, until the culture was approximately 100% confluent.

Similarly to Example 4, the CHO cells and the polyethylene oxide oleylether (n=90, average molecular weight of 4400)-EGFP conjugates were incubated, and then observed under a confocal laser scanning microscope. The results are shown in Table 1. As a result, fluorescence from EGFP was observed on the cell membranes of all of the CHO cells treated with a solution of the polyethylene oxide oleylether (n=90, average molecular weight of 4400)-EGFP conjugates. Therefore, it was verified that the conjugate can be anchored to cells other than mouse cells.

Example 6

Anchoring of Polyethylene Oxide Oleylether (n=90, Average Molecular Weight of 4400)-EGFP Conjugates to Suspended Cells Cultivation of 32D, Ba/F3 and 9E10 cells Mouse myeloid cell line 32D and mouse pro-B cell line Ba/F3 were cultured at 37° C. under 5% $CO_2$ concentration using RPMI media supplemented with interleukin-3 at a final concentration of 2 ng/mL and 10% fetal calf serum. Mouse hybridoma 9E10 was cultured at 37° C. under 5% $CO_2$ concentration using RPMI 1640 media ("Nissui" powder, NISSUI PHARMACEUTICAL CO., LTD., Cat# 05918) supplemented with 10% fetal calf serum. A stock solution of the polyethylene oxide oleylether (n=90, average molecular weight of 4400)-EGFP conjugates was diluted 20 fold with RPM11640 media to prepare a solution of E290-EGFP conjugates. 32D, Ba/F3 and 9E10 cells (hereinafter, generically called as "suspended cells") were centrifuged to collect $1 \times 10^6$ cells. Each of the cell was centrifuged for washing with 13 mL of phosphate buffered saline. 0.1 mL of the solution of the polyethylene oxide oleylether (n=90, average molecular weight of 4400)-EGFP conjugates was added to each cell pellet, and then incubated at 37° C. for 5 min. Then the cells were centrifuged for washing once with 13 mL of phosphate buffered saline, and then 1 mL of phosphate buffered saline was added to each cell pellet.

Figure 3:
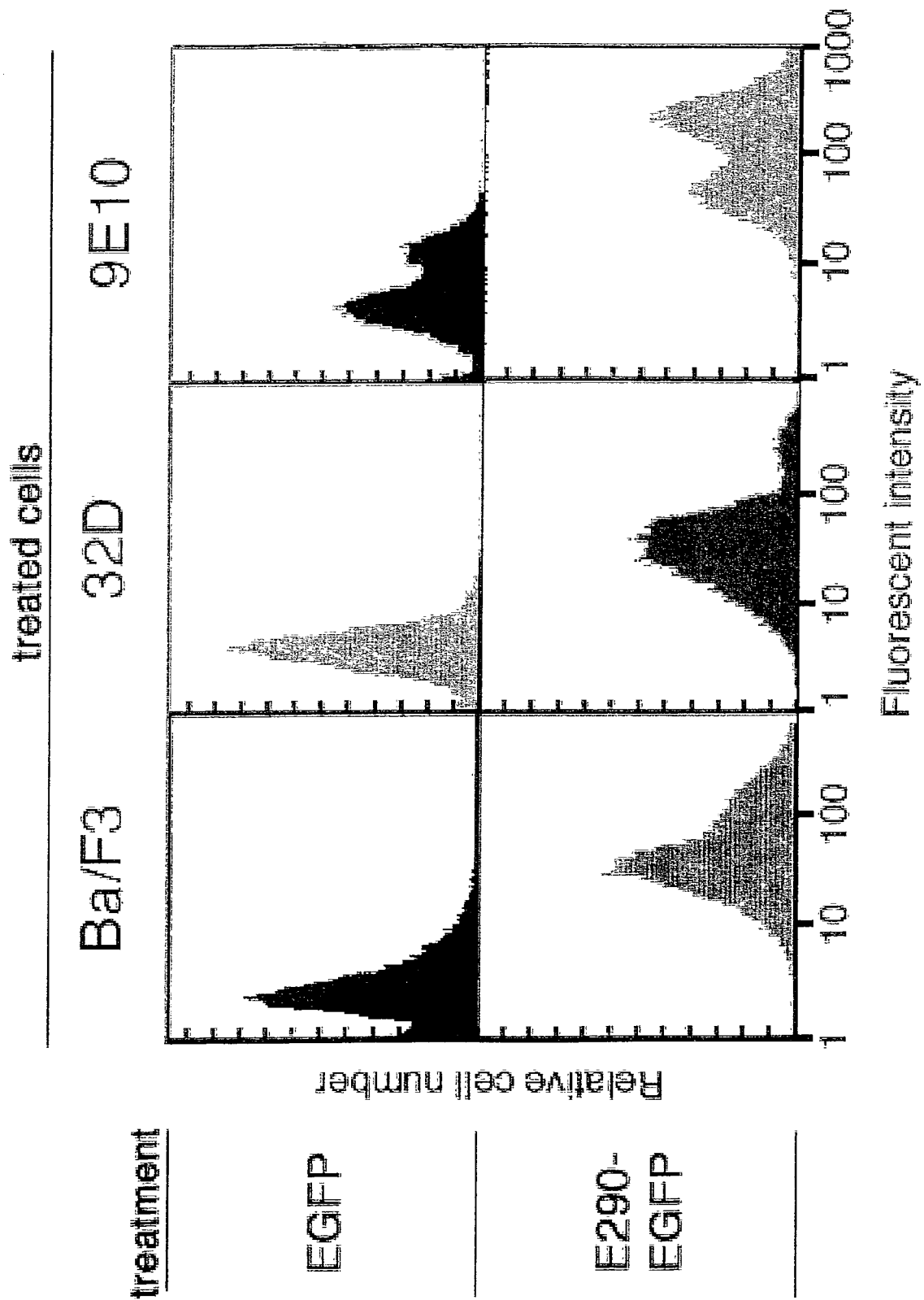
FIG. 3 shows the results of observation using a flow cytometer of suspended cells (Example 6) whose membranes were modified with polyethylene oxide oleylether (n=90, average molecular weight of 4,400)-EGFP conjugates.

Respective treated cell suspensions were observed under a flow cytometer (Coulter, EPICS-C). The results are shown in Table 2 and FIG. 3. As a result, compared to suspended cells treated only with EGFP, an increased number of the cells with a stronger fluorescence intensity was observed when the cells were treated with the polyethylene oxide oleylether-EGFP conjugates. These results indicate that EGFP was provided to the membranes of all the suspended cells by treatment with the polyethylene oxide oleylether-EGFP conjugates. Thus, it was verified that the polyethylene oxide oleylether-EGFP can be anchored to suspended cells.

Example 7

Anchoring of Polyethylene Oxide Oleylether (n=15; Average Molecular Weight of 1100)-biotin Conjugates to Mouse Fibroblast Cell Line NIH$_3$T3.

Each activated polyethylene oxide oleylether was obtained in a manner similar to Synthesis Example 1. Then, a stock solution of each polyethylene oxide oleylether-biotin conjugate was obtained in a manner similar to Example 1. Further, each polyethylene oxide oleylether-biotin conjugate was allowed to react with NIH$_3$T3 cells in a manner similar to Example 2, and then with fluorescein-labeled streptavidin. The cells were observed under a confocal laser scanning microscope to examine the modification of the cell membranes. The results are shown in Table 1. As a result, fluorescence from fluorescein was observed for the cell membranes of all the NIH$_3$T3 cells treated with the solution of the polyethylene oxide oleylether-biotin conjugates.

Example 8

Anchoring of Polyethylene Oxide Oleylether (n=40; Average Molecular Weight of 2250)-biotin Conjugates to Mouse Fibroblast Cell Line NIH$_3$T3

Polyethylene oxide oleylether (n=40: average molecular weight of 2250)-biotin conjugates were obtained in a manner similar to Example 7, and then incubated with NIH$_3$T3 in a similar manner. Subsequently, the cells were allowed to react with fluorescein-labeled streptavidin, and then observed under a confocal laser scanning microscope to examine the modification of the cell membranes.

Example 9

Anchoring of Polyethylene Oxide Oleylether (n=180; Average Molecular Weight of 8400)-biotin Conjugates to Mouse Fibroblast Cell Line NIH$_3$T3

Polyethylene oxide oleylether (n=180: average molecular weight of 8400)-biotin conjugates were obtained in a manner similar to Example 7, and then incubated with NIH$_3$T3 in a similar manner. Subsequently, the cells were allowed to react with fluorescein-labeled streptavidin, and then observed under a confocal laser scanning microscope to examine the modification of the cell membranes.

Figure 4:
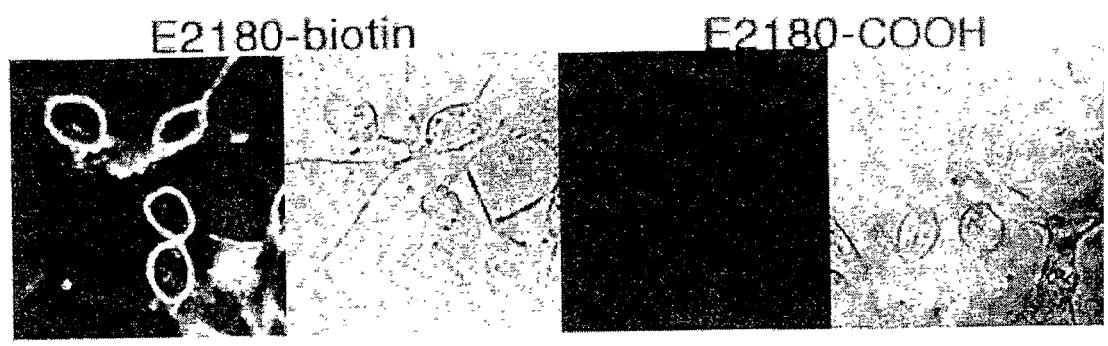
FIG. 4 shows microscopic photographs of mouse fibroblast cell line NIH3T3 (Example 9) whose membranes were modified with fluorescein-labeled streptavidin bound to polyethylene oxide oleylether (n=180, average molecular weight of 8,400)-biotin conjugates.

The results of Examples 7 to 9 are shown in Table 1. The results of Example 9 are shown in FIG. 4. Fluorescence from fluorescein was observed on the cell membranes of all the NIH$_3$T3 cells treated with the solution of the polyethylene oxide oleylether-biotin conjugates. Therefore, it was verified that even when the number of added moles of ethylene oxide of polyethylene oxide is changed from 15 to 180, any compounds can be anchored to cell membranes.

Example 10

Anchoring of Polyethylene Oxide Stearyl Ether (n=15: Average Molecular Weight of 1100)-biotin Conjugates to Mouse Fibroblast Cell Line NIH$_3$T3

Activated polyethylene oxide stearyl ether (n=15, average molecular weight of 1100) was obtained in a manner similar to Synthesis Example 1, and then a stock solution of the polyethylene oxide stearyl ether (n=15, average molecular weight of 1100)-biotin conjugates was obtained in a manner similar to Example 1. Further, in a manner similar to Example 2, the polyethylene oxide stearyl ether (n=15, average molecular weight of 1100)-biotin conjugates were incubated with NIH$_3$T3, allowed to react with fluorescein-labeled streptavidin, and then observed under a confocal laser scanning microscope to examine the modification of the cell membranes. The results are shown in Table 1. As a result, fluorescence from fluorescein was observed on the cell membranes of the NIH$_3$T3 cells treated with the solution of the polyethylene oxide stearyl ether-biotin conjugates. It was verified that even when unsaturated oleyl groups are changed to saturated stearyl groups in the aliphatic hydrocarbon groups, the compounds can be anchored to cell membranes. However, fluorescence observed from the compound containing oleyl groups was stronger than that from the compound containing stearyl groups, suggesting that the compound containing oleyl groups is more preferred for the cell line used.

Synthesis Example 2

Synthesis of Fluorescent-Labeled (Fluorescein) Polyethylene Oxide-Modified Dioleoyl Phosphatidyl Ethanolamine 5 g (1 mmol) of fluorescent-labeled (fluorescein)-polyethylene oxide (average molecular weight of 5000) with the activated end was obtained in a manner similar to Synthesis Example 1, and then dissolved in 10 mL of chloroform to obtain a solution of the activated fluorescent-labeled (fluorescein) polyethylene oxide. 0.8 g (1.1 mmol) of dioleoyl phosphatidyl ethanolamine and 0.1 g (1.1 mmol) of triethylamine were dissolved in 10 mL of chloroform, added to the solution of the activated fluorescent-labeled (fluorescein)-polyethylene oxide, and then allowed to react at 40° C. After the reaction, filtration was performed to remove unreacted dioleoyl phosphatidyl ethanolamine, followed by crystallization using 100 mL of ethyl acetate and 100 mL of hexane to obtain 4.8 g of crystals.

Example 11

Anchoring of Fluorescent-Labeled (Fluorescein)-Polyethylene Oxide-Modified Dioleoyl Phosphatidyl Ethanolamine to Mouse Fibroblast Cell Line NIH$_3$T3

Figure 5:
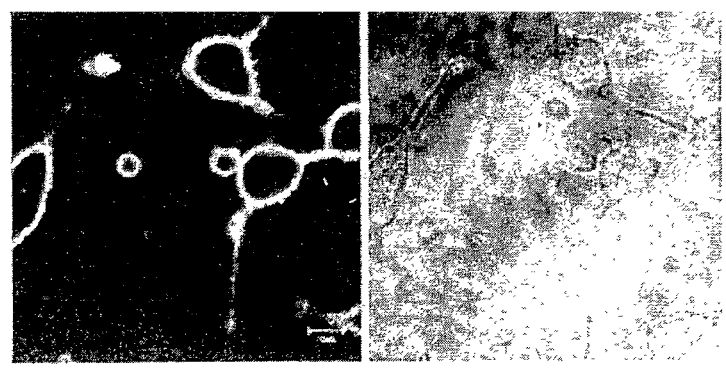
FIG. 5 shows microscopic photographs of mouse fibroblast cell line NIH3T3 (Example 11) whose membranes were modified with fluorescent-labeled (fluorescein)-polyethylene oxide-modified dioleoyl phosphatidyl ethanolamine.

In a manner similar to Example 2, a solution of the fluorescent-labeled (fluorescein)-polyethylene oxide-modified dioleoyl phosphatidyl ethanolamine and NIH$_3$T3 were incubated, and then observed under a confocal laser scanning microscope to examine the modification of the cell membranes. The results are shown in Table 1 and FIG. 5. Fluorescence from fluorescein was observed on the cell membranes of all the NIH$_3$T3 cells treated with the fluorescent-labeled (fluorescein)-polyethylene oxide-modified dioleoyl phosphatidyl ethanolamine, which verified that the compound can be anchored to cell membrane. Moreover, the compound gave longer retention time of anchoring to the cell membranes compared to the cells in which polyethylene oxide oleylether-biotin conjugate was used. It was thus verified that more stable anchoring to cell membranes is achievable by using the polyethylene oxide-modified dioleoyl phosphatidyl ethanolamine compound having two chains of aliphatic hydrocarbon groups.

Example 12

Anchoring of Amino Polyethylene Oxide Oleylether (n=90, Average Molecular Weight of 4400)-biotin Conjugate to Mouse Fibroblast Cell Line $NIH_3T3$ Activated amino polyethylene oxide oleylether was obtained in a manner similar to Synthesis Example 1 using amino polyethylene oxide oleylether (n=90, average molecular weight of 4400). A stock solution of the amino polyethylene oxide oleylether-biotin conjugates was prepared in a manner similar to Example 4 using the resulting activated amino polyethylene oxide oleylether, and then anchoring to the cell membranes of $NIH_3T3$ was performed. Then, the cells were allowed to react with fluorescein-labeled streptavidin, and then observed under a confocal laser scanning microscope for examination. The results are shown in Table 1. As a result, it was verified that when the mode of binding with biotin was changed to the amide bond using the amino polyethylene oxide oleylether, the effect of anchoring to cell membranes was remain unchanged and still excellent.

Example 13 (Comparative Example)

Examination of the Presence or Absence of Non-specific Binding of Fluorescein-labeled Streptavidin to Polyethylene Oxide Oleylether (n=90, Average Molecular Weight of 4400)

A reaction solution was prepared by adding 0.02 mL of 1M Tris buffer (pH 8.0) and 0.78 mL of phosphate buffered saline (the same as above) for tissue culture to the solution of the activated polyethylene oxide oleylether obtained in Synthesis Example 1. The reaction solution was stirred and then allowed to stand at room temperature (about 25° C.) for 1 hour to prepare a stock solution of the polyethylene oxide oleylether succinate from the reaction solution. In a manner similar to Example 2, the stock solution of the polyethylene oxide oleylether succinate was diluted 100 fold with Dulbecco's Modified Eagle's Medium, and then a solution of the polyethylene oxide oleylether succinate and a solution of biotin-$NH_2$ were prepared. $NIH_3T3$ cells were similarly treated and allowed to react with fluorescein-labeled streptavidin, and then observed under a confocal laser scanning microscope. The results are shown in Table 1. As a result, no fluorescence from fluorescein was observed for all the cells treated with the solution of polyethylene oxide oleylether succinate. Accordingly, it was demonstrated that fluorescein-labeled streptavidin failed to bind non-specifically to the cells treated with polyethylene oxide oleylether succinate.

Example 14 (Comparative Example)

Examination of the Presence or Absence of Non-Specific Binding of Biotin-$NH_2$ to Cell Membrane 1 nmol EZ-Link™ Biotin-PEO-Amine was dissolved in 0.2 mL of dimethyl sulfoxide to prepare a Biotin-PEO-Amine solution. A mixed solution was prepared by adding 0.02 mL of 1M Tris buffer (pH$_{8.0}$) and 0.78 mL of phosphate buffered saline (the same as above) for tissue culture to the total volume of the Biotin-PEO-Amine solution. The mixed solution was stirred and then allowed to stand at room temperature (about 25° C.) for 1 hour. After the standing, the mixed solution was used as a stock solution of biotin-$NH_2$. In a manner similar to Example 2, the stock solution of the biotin-$NH_2$ was diluted 100 fold with Dulbecco's Modified Eagle's Medium to prepare a solution of the biotin-$NH_2$. $NIH_3T3$ cells were similarly treated and allowed to react with fluorescein-labeled streptavidin, and then observed under a confocal laser scanning microscope. The results are shown in Table 1.

As a result, no fluorescence from fluorescein was observed for all the cells treated with the biotin-$NH_2$ solution. It was thus demonstrated that biotin itself did not bind to the cells.

Example 15 (Comparative Example)

Anchoring of Oleic Acid-biotin to Mouse Fibroblast Cell Line $NIH_3T3$

Synthesis Example 3

Preparation of a Solution of Oleic Acid-biotin and a Solution of Polyethylene Oxide (n=114, Average Molecular Weight of 5000)-biotin Activated oleic acid (molecular weight of 379) was obtained in a manner similar to Synthesis Example 1. Using the resulting activated oleic acid (molecular weight of 379) and activated polyethylene oxide (n=114, average molecular weight of 5000), a solution of oleic acid-biotin and a solution of polyethylene oxide (n=114, average molecular weight of 5000)-biotin were prepared in a manner similar to Example 1. By using the resulting solution of the activated oleic acid (molecular weight of 379) and the solution of the activated polyethylene oxide, incubation was performed with $NIH_3T3$ in a manner similar to Example 2, and then allowed to react with fluorescein-labeled streptavidin and observed under a confocal laser scanning microscope for examination of the modification of the cell membranes. The results are shown in Table 1. As a result, no fluorescence from fluorescein was observed for all the cells treated with the oleic acid-biotin solution and the activated polyethylene oxide solution.

Example 16 (Comparative Example)

Anchoring of Polyethylene Oxide (n=114, Average Molecular Weight of 5000)-biotin to Mouse Fibroblast Cell Line $NIH_3T3$.

Figure 6:
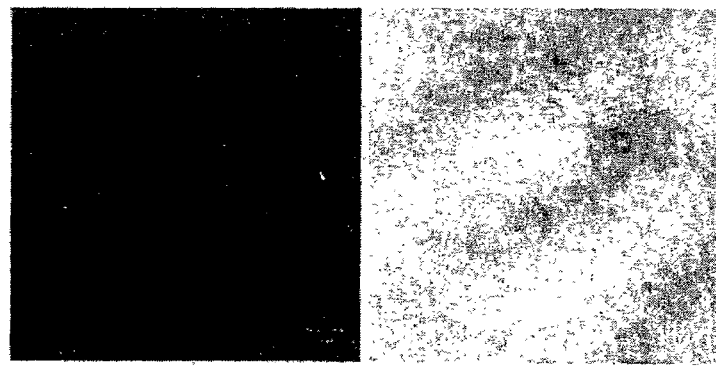
FIG. 6 shows microscopic photographs of mouse fibroblast cell line NIH3T3 (Example 16: Comparative example) for which membrane modification was attempted with polyethylene oxide (n=114, average molecular weight of 5,000)-biotin.

Polyethylene oxide (n=114, average molecular weight of 5000) was synthesized in a manner similar to Synthesis Example 1, and purified by using an ion exchange column to obtain an activated polyethylene oxide. The resulting activated polyethylene oxide (n=114, average molecular weight of 5000) was used for incubation with $NIH_3T3$ in a manner similar to Example 2. The cells were then allowed to react with fluorescein-labeled streptavidin, and then observed under a confocal laser scanning microscope to examine the modification of the cell membranes. The results are shown in Table 1 and FIG. 6. As a result, no fluorescence from fluorescein was observed for all the cells treated with the solution of the polyethylene oxide (n=114, average molecular weight of 5000)-biotin. From the results of Examples 15 and 16, it was demonstrated that compounds containing either an aliphatic hydrocarbon group or a hydrophilic group are not applicable for cell membrane modification, and coexistence of both of hydrophobic and hydrophilic groups is essential.

Example 17

Anchoring of Polyethylene Oxide Nonylphenyl Ether (n=40, Average Molecular Weight of 2160)-biotin Conjugate to Mouse Fibroblast Cell Line $NIH_3T3$ A solution of activated polyethylene oxide nonylphenyl ether was obtained in a manner similar to Synthesis Example 1. Then polyethylene oxide nonylphenyl ether (n=40, average molecular weight of 2160)-biotin conjugate was prepared in a manner similar to Example 1 and then allowed to react with $NIH_3T3$ cells in a manner similar to Example 2. The cells were allowed to further react with fluorescein-labeled streptavidin, and then observed under a confocal laser scanning microscope to examine the modification of the cell membranes. The results are shown in Table 1. As a result, no fluorescence from fluorescein was observed for all the cells treated with the solution of the polyethylene oxide nonylphenyl ether (n=40, average molecular weight of 2160)-biotin. It was demonstrated that compounds containing bulky substituent

| | Chemical structure | Carbon number | EO mole number | Physiologically active substance | Cell | Anchoring to cell surface |
|---|---|---|---|---|---|---|
| Example 2 | 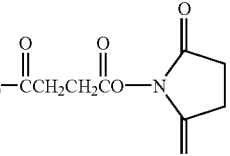 | C18:1 | 90 | Biotin | Mouse fibroblasts NIH3T3 | ++ |
| Example 4 | 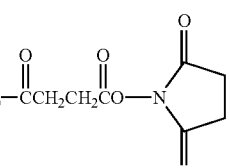 | C18:1 | 90 | EGFP | Mouse fibroblasts NIH3T3 | ++ |
| Example 5 | 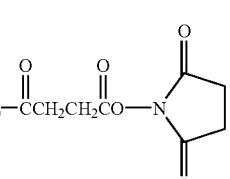 | C18:1 | 90 | EGFP | Chinese hamster ovarian follicle cells CHO | ++ |
| Example 6 | 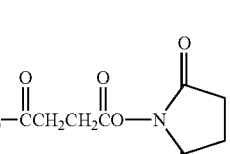 | C18:1 | 90 | EGFP | Suspended cell | ++ |
| Example 7 | 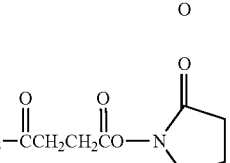 | C18:1 | 15 | Biotin | Mouse fibroblasts NIH3T3 | ++ |
| Example 8 | 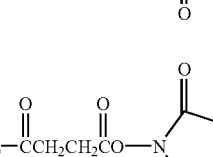 | C18:1 | 40 | Biotin | Mouse fibroblasts NIH3T3 | ++ |

-continued

| Chemical structure | Carbon number | EOmole number | Physiologically active substance | Cell | Anchoring to cell surface |
|---|---|---|---|---|---|
| Example 9: CH₃(CH₂)₈=(CH₂)₉O—(CH₂CH₂O)₁₀₀CCH₂CH₂CO—N(succinimide) | C18:1 | 180 | Biotin | Mouse fibroblasts NIH3T3 | ++ |
| Example 10: CH₃(CH₂)₁₇O—(CH₂CH₂O)₁₈₀CCH₂CH₂CO—N(succinimide) | C18:0 | 15 | Biotin | Mouse fibroblasts NIH3T3 | + |
| Example 11: CH₃(H₂C)₈=(CH₂)₉—CO—CH₂ / CH₃(H₂C)₈=(CH₂)₉—CO—CH / CH₃OPO(CH₂)₂NHC(CH₂)₂CO(CH₂CH₂O)₁₁₃CH₂CH₂NH—FL | C18:1 | 113 | Fluorescein | Mouse fibroblasts NIH3T3 | ++ |
| Example 12: CH₃(CH₂)₈=(CH₂)₈O—(CH₂CH₂O)₉₀CH₂CH₂NH—CCH₂CH₂CO—N(succinimide) | C18:1 | 90 | Biotin | Mouse fibroblasts NIH3T3 | ++ |
| Example 15: CH₃(CH₂)₈=(CH₂)₈—CO—N(succinimide) | C18:1 | 0 | Biotin | Mouse fibroblasts NIH3T3 | − |
| Example 16: HO—(CH₂CH₂O)₁₁₃—CCH₂CH₂CO—N(succinimide) | — | 113 | Biotin | Mouse fibroblasts NIH3T3 | − |
| Example 17: C₉H₁₉—C₆H₆O—(CH₂CH₂O)₄₀—CCH₂CH₂CO—N(succinimide) | C15 (Phenyl) | 40 | Biotin | Mouse fibroblasts NIH3T3 | − |

In Table 1, ++ represents that significantly strong fluorescence activity was observed on the cell membranes of all the cells within the field of view (1000 magnifications); +represents that fluorescence activity was observed on the cell membranes of all the cells within the field of view (1000 magnifications); and – represents that almost no fluorescence activity was observed on the cell membranes of all the cells in the field of view (1000 magnifications).

TABLE 2

| Cell line | Treated only with green fluorescent protein EGFP | Treated with polyethylene oxide octadecyl ether-green fluorescent protein EGFP conjugate |
|---|---|---|
| Ba/F3 | 2.5 | 36.7 |
| 32D | 3.7 | 30.1 |
| 9E10 | 4.5 | 49.6 |

Evaluation: a relative value of fluorescence intensity of cells

INDUSTRIAL APPLICABILITY

The cells of the present invention have cell membranes stably modified with a substance to be modified, such as a physiologically active substance or a probe, and the cells are not damaged by the modification of the cell membrane. Accordingly, the cells have a characteristic feature in that they can stably express a desired property based on the modification of the cell membrane for a prolong period of time. Moreover, the modification method for cell membranes provided by the present invention has a feature that it can efficiently and stably provide cells having the above feature.

What is claimed is:

1. A modified cell having a cell membrane to which is non-covalently bound a reaction product of an amphipathic compound and a physiologically active substance or a probe, wherein said amphipathic compound is represented by the following formula (1):

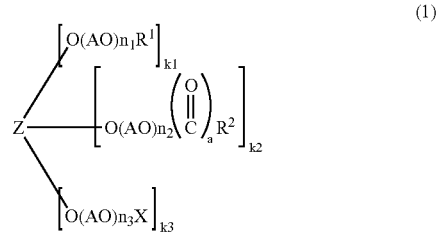

(1)

wherein Z represents a residue of a compound having 2 to 10 hydroxyl groups; AO represents an oxyalkylene group having 2 to 4 carbon atoms; $R^1$ represents a hydrogen atom or a hydrocarbon group having 1 to 3 carbon atoms; $R^2$ represents a residue of a compound having an aliphatic hydrocarbon group having 7 to 22 carbon atoms; X represents a group having at least one reactive functional group selected from succinimide group, maleimide group, amino group, carboxyl group, aldehyde group, glycidyl group, and thiol group; "a" represents 0 or 1; n1, n2, and n3 represent an average number of added moles of an oxyalkylene group having 2 to 4 carbon atoms, and each numerical number represented by n1, n2, n3, k1, k2, and k3 satisfies the following conditions:

$0 \leq n1, n2 \leq 500, 2 \leq n3 \leq 500$, and $2 \leq n1+n2+n3 \leq 500$ $0 \leq k1 \leq 8, 1 \leq k2 \leq 4, 1 \leq k3 \leq 4$, and $2 \leq k1+k2+k3 \leq 10$; and wherein the physiologically active substance or probe reacts with the amphipathic compound at group X to produce the reaction product; and wherein the reaction product is non-covalently bound to the cell membrane through at least a portion of $R^2$.

2. The cell according to claim 1, wherein the cell is an animal cell.

3. The cell according to claim 1, wherein $R^2$ is a residue of a compound having at least one linear aliphatic hydrocarbon group having 11 to 18 carbon atoms.

4. The cell according to claim 1, wherein $R^2$ is a residue of a compound having at least one oleyl group or an unsaturated aliphatic hydrocarbon group having 17 carbon atoms.

5. The cell according to claim 1, wherein $R^2$ is a group represented by the following formula (2):

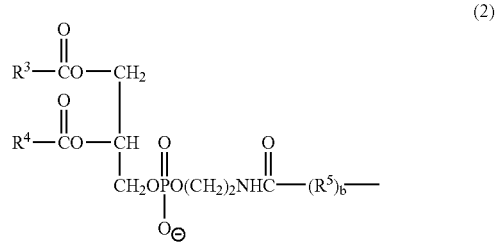

(2)

wherein each of $R^3$ and $R^4$ independently represents a hydrocarbon group having 7 to 21 carbon atoms; $R^5$ represents a hydrocarbon group having 2 to 4 carbon atoms; and b represents 0 or 1.

6. A method for modifying cell membranes, which comprises:

(1) reacting a physiologically active substance or a probe with an amphipathic compound according to formula (1):

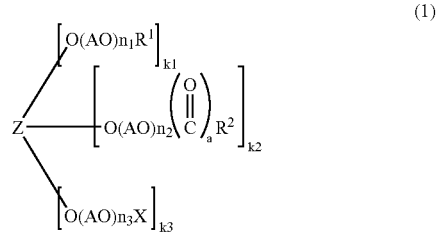

(1)

wherein Z represents a residue of a compound having 2 to 10 hydroxyl groups; AO represents an oxyalkylene group having 2 to 4 carbon atoms; $R^1$ represents a hydrogen atom or a hydrocarbon group having 1 to 3 carbon atoms; $R^2$ represents a residue of a compound having an aliphatic hydrocarbon group having 7 to 22 carbon atoms; X represents a group having at least one reactive functional group selected from succinimide group, maleimide group, amino group, carboxyl group, aldehyde group, glycidyl group, and thiol group; "a"

represents 0 or 1; n1, n2, and n3 represent an average number of added moles of an oxyalkylene group having 2 to 4 carbon atoms, and each numerical number represented by n1, n2, n3, k1, k2, and k3 satisfies the following conditions:

$0 \leq n1, n2 \leq 500, 2 \leq n3 \leq 500$, and $2 \leq n1+n2+n3 \leq 500$ $0 \leq k1 \leq 8, 1 \leq k2 \leq 4, 1 \leq k3 \leq 4$, and $2 \leq k1+k2+k3 \leq 10$; and wherein the physiologically active substance or probe reacts with the amphipathic compound at group X to produce the reaction product; and (2) non-covalently binding a reaction product obtained in (1), through at least a portion of $R^2$, to a cell membrane.

7. The method for modifying cell membranes according to claim 6, wherein $R^2$ is a residue of a compound having at least one oleyl group or an unsaturated aliphatic hydrocarbon group having 17 carbon atoms.

8. The method for modifying cell membranes according to claim 6, wherein $R^2$ is a group represented by the following formula (2):

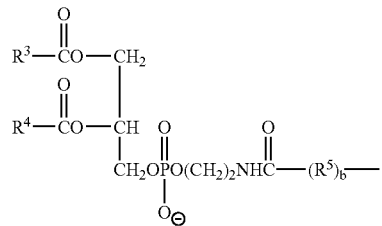

(2)

wherein each of $R^3$ and $R^4$ independently represents a hydrocarbon group having 7 to 21 carbon atoms; $R^5$ represents a hydrocarbon group having 2 to 4 carbon atoms; and b represents 0 or 1.

* * * * *